United States Patent [19]

Ishitani et al.

[11] 4,302,312
[45] Nov. 24, 1981

[54] DEVICE FOR PRODUCING CONTROL SIGNAL FOR FEEDBACK CONTROL OF AIR/FUEL MIXING RATIO

[75] Inventors: Shigeo Ishitani, Yokosuka; Shinji Kimura, Yokohama; Hiroshi Takao, Kamakura; Masaaki Uchida, Yokohama, all of Japan

[73] Assignee: Nissan Motor Co., Ltd., Yokohama, Japan

[21] Appl. No.: 172,227

[22] Filed: Jul. 25, 1980

[30] Foreign Application Priority Data

Jul. 28, 1979 [JP] Japan .................. 54-95574

[51] Int. Cl.³ ........................... G01N 27/58
[52] U.S. Cl. .............................. 204/195 S
[58] Field of Search ............... 204/195 S, 1 S; 123/440, 489; 60/276

[56] References Cited

U.S. PATENT DOCUMENTS

4,207,159  6/1980  Kimura et al. .......... 204/195 S
4,224,113  9/1980  Kimura et al. .......... 204/1 T

*Primary Examiner*—G. L. Kaplan
*Attorney, Agent, or Firm*—Schwartz, Jeffery, Schwaab, Mack, Blumenthal & Koch

[57] ABSTRACT

A device comprising an oxygen-sensitive element to be disposed in combustion gas exhausted from a combustor to detect deviation of actual air/fuel mixing ratio of a mixture supplied to the combustor from a stoichiometric ratio. The element is a combination of two oxygen concentration cells each having a solid electrolyte layer, a measurement electrode layer formed on one side of the electrolyte layer and a reference electrode layer formed on the opposite side and covered with a shield layer. The device includes DC power supply means for forcing a current to flow through the solid electrolyte layer of each cell thereby to cause migration of oxygen ions therethrough, from the measurement electrode to the reference electrode in one cell and reversely in the other cell, and a circuit to make a comparison between first and second output voltages respectively developed by the first and second cells to examine which one of these two output voltages is higher than the other and produce a control signal according to the result of the comparison. The signal-producing function is not influenced by the temperature of the element so that a correct control signal can be produced even when the element is not yet sufficiently heated.

10 Claims, 13 Drawing Figures

DEVICE FOR PRODUCING CONTROL SIGNAL FOR FEEDBACK CONTROL OF AIR/FUEL MIXING RATIO

BACKGROUND OF THE INVENTION

This invention relates to a device for producing a control signal for feedback control of the air/fuel ratio of an air-fuel mixture supplied to a combustor, such as the combustion chambers of an internal combustion engine, based on the concentration of oxygen in a combustion gas exhausted from the combustor.

In recent internal combustion engines, particularly in automotive engines, there has developed a marked tendency to very minutely control the air/fuel mixing ratio to improve the efficiency of the engines and reduce the emission of noxious components of exhaust gas. In many cases it is desirable to feed an engine with a stoichiometrical air-fuel mixture, and it has become standard practice to perform feedback control of air/fuel mixing ratio with the aim of maintaining a stoichiometric air/fuel ratio by using an exhaust gas sensor which provides a feedback signal indicative of the composition of an air-fuel mixture actually supplied to the engine.

For example, in an automotive engine system using a so-called three-way catalyst which can catalyze both reduction of nitrogen oxides and oxidation of carbon monoxide and unburned hydrocarbons contained in the exhaust gas, it is quite important to always feed the engine with an exactly stoichiometrical air-fuel mixture because this catalyst performs most effectively in an exhaust gas produced by combustion of a stoichiometrical air-fuel mixture. Accordingly, in this engine system it becomes indispensable to perform feedback control of the air/fuel mixing ratio.

Usually, conventional feedback air/fuel ratio control systems aiming at a stoichiometric air/fuel ratio utilize an oxygen sensor that operates on the principle of a concentration cell as an exhaust gas sensor to provide a feedback signal. This type of oxygen sensor has a layer of an oxygen ion conductive solid electrolyte, such as zirconia stabilized with calcia, formed into the shape of a tube closed at one end. A measurement electrode layer is porously formed on the outer side of the solid electrolyte tube and a reference electrode layer is formed on the inner side of the tube. When there is a difference in oxygen partial pressure between the reference electrode side and measurement electrode side of the solid electrolyte layer, this sensor generates an electromotive force between the two electrode layers. As an exhaust gas sensor, the measurement electrode layer is exposed to an engine exhaust gas while the reference electrode layer on the inside is exposed to atmospheric air utilized as the source of a reference oxygen partial pressure. In this environment the magnitude of an electromotive force generated by the oxygen sensor exhibits a large and rapid change between a maximally high level and a minimally low level upon the occurrence of a change in the air/fuel ratio of a mixture fed to the engine across the stoichiometric air/fuel ratio. Accordingly it is possible to produce a fuel feed rate control signal based on the result of a comparison of the output of the oxygen sensor with a reference voltage which is set at the middle of the high and low levels of the sensor output.

However, this type of oxygen sensor has disadvantages such as: significant temperature dependence of its output characteristic: necessity of using a reference gas such as air; difficulty in reducing its size; and poor mechanical strength.

To eliminate these disadvantages, U.S. patent application Ser. No. 12,763 filed Feb. 16, 1979 and now U.S. Pat. No. 4,207,159 discloses an advanced oxygen sensor, which is of a concentration cell type having a flat solid electrolyte layer with reference and measurement electrode layers formed respectively on the two opposite sides thereof and a shield layer formed on the reference electrode side of the solid electrolyte layer so as to cover the reference electrode layer entirely. Either the shield layer or the solid electrolyte layer is made rigid and thick enough to serve as a substrate, and each of the remaining three layers can be formed as a thin film-like layer. This sensor does not use any reference gas. Instead, a DC power supply is connected to this sensor so as to force a current to flow through the solid electrolyte layer between the reference and measurement electrode layers thereby to cause migration of oxygen ions through the solid electrolyte layer in a selected direction and, as a consequence, establish a reference oxygen partial pressure at the interface between the solid electrolyte layer and the reference electrode layer. (The particulars of this oxygen sensor will be described hereinafter.)

When disposed in an engine exhaust gas, this advanced oxygen sensor exhibits an output characteristic generally similar to that of the conventional oxygen sensor having a tubular solid electrolyte. Accordingly, this oxygen sensor is serviceable as a device to provide a feedback signal in an air/fuel ratio control system aiming at a stoichiometric air/fuel ratio. Moreover, this sensor has advantages, such as: lack of need for any reference gas; possibility of making it small in size; and good resistance to shocks and vibrations. However, the output characteristic of this oxygen sensor too is significantly affected by temperature. Particularly, when the temperature of the sensor is below about 500° C. the output characteristic changes such that it becomes difficult to make a comparison between a reference voltage of an adequate level and the output of the sensor. This is a matter of great inconvenience in practical air/fuel ratio control systems for automotive engines.

SUMMARY OF THE INVENTION

It is an object of the present invention to provide a device for producing a control signal for feedback control of the air/fuel ratio of an air-fuel mixture supplied to a combustor, such as combustion chambers of an internal combustion engine. The device includes an improved oxygen-sensitive element to be disposed in a combustion gas exhausted from the combustor and which can produce an air/fuel ratio control signal in accordance with the deviation of an actual air/fuel ratio of the air-fuel mixture from a stoichiometric air/fuel ratio with good stability and without being influenced by temperature even when the temperature is considerably low.

A device according to the invention comprises an oxygen-sensitive element which is to be disposed in a combustion gas exhausted from a combustor and comprises first and second concentration cells each composed of: a layer of an oxygen ion conductive solid electrolyte; a measurement electrode layer formed on one side of the solid electrolyte layer; a reference electrode layer formed on the other side of the solid electrolyte layer; and a shield layer formed on the reference electrode side of the solid electrolyte layer such that macroscopically the reference electrode layer is entirely shielded from an environmental atmosphere by the shield layer and the solid electrolyte layer. At least one of the shield layer and the solid electrolyte layer has a microscopically porous and gas permeable structure. The device further comprises DC power supply means for forcing a first DC current of a predetermined intensity to flow through the solid electrolyte layer of the first concentration cell from the reference electrode layer towards the measurement electrode layer and a second DC current of a predetermined intensity to flow through the solid electrolyte layer of the second concentration cell from the measurement electrode layer towards the reference electrode layer. A signal-producing circuit has comparing means for making a comparison between a first output voltage developed between the reference and measurement electrode layers of the first cell and a second output voltage developed between the reference and measurement electrode layers of the second cell to examine which one of the first and second output voltages is higher than the other. Signal-generating means is provided for producing an air/fuel ratio control signal which varies according to a high-low relationship between the first and second output voltages examined by the comparing means.

The flow of a DC current in each cell causes migration of oxygen ions through the solid electrolyte layer between the reference and measurement electrode layers in a direction reversely of the direction of the current flow. As a consequence, in the first cell a reference oxygen pressure of a relatively high magnitude can be maintained on the reference electrode side, whereas in the second cell a reference oxygen partial pressure of a relatively low magnitude can be maintained on the reference electrode side. Therefore, in a combustion gas produced from a fuel-rich air-fuel mixture the first output voltage becomes higher than the second output voltage, but in a combustion gas produced from a lean mixture containing excess air the first output voltage becomes lower than the second output voltage. At a stoichiometric air/fuel ratio, each of the first and second output voltages exhibits a sharp change between a high level and a low level. Since the output characteristics of the first and second cells are similarly influenced by the temperature of the oxygen-sensitive element, a high-low relationship between the first output voltage and the second output voltage remains unchanged even though the temperature of the element varies considerably. Therefore, this device can produce a control signal for feedback control of the air/fuel ratio aiming at a stoichiometric air/fuel ratio with good stability and accuracy even when the combustion gas temperature is considerably low.

In principle, the first and second oxygen concentration cells in the oxygen-sensitive element may be separated from each other, but in practice it is preferred to unite the two cells into a single element by uniting either the shield layers or the solid electrolyte layers of the two cells into a single layer which is made rigid and thick enough to serve as a structurally basic member or substrate of the entire element. The oxygen-sensitive element can be designed in a variety of forms as will be illustrated in the description of the preferred embodiments.

For example, the signal-generating means in the present invention can be composed of a combination of a voltage divider to which a constant source voltage is applied and a switching transistor the base of which is connected to the output terminal of the comparing means.

DETAILED DESCRIPTION OF THE INVENTION

Prior to a detailed description of preferred embodiments of the present invention, a conventionally popular oxygen sensor will be described briefly, and then an advanced oxygen sensing element according to U.S. Pat. No. 4,207,150 will be described somewhat in detail.

Figure 1:
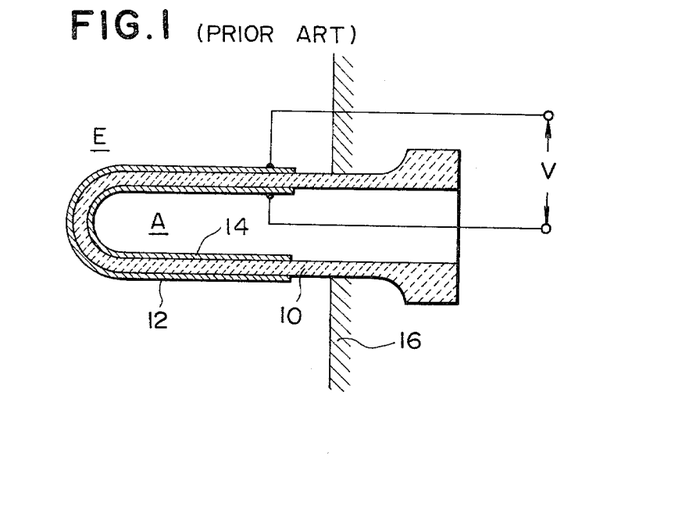
FIG. 1 is a schematic and sectional view of a conventional oxygen sensor.

FIG. 1 shows the construction of a conventional oxygen sensor currently used in automobile exhaust systems to detect the air/fuel ratio of air-fuel mixtures supplied to the engines. This oxygen sensor has a layer 10 of an oxygen ion conductive solid electrolyte, such as $ZrO_2$ stabilized with CaO or $Y_2O_3$, which is formed into the shape of a tube closed at one end. Formed on the outer side of the solid electrolyte tube 10 is a thin and microscopically porous measurement electrode layer 12 which is exposed to an exhaust gas E when the sensor is attached to an exhaust pipe 16 for an automotive engine. Formed on the inner side of the solid electrolyte tube 10 is a thin and microscopically porous reference electrode layer 14 which is isolated from the exhaust gas and exposed to atmospheric air A utilized as the source of a reference oxygen partial pressure. Usually platinum is used as the material for the electrode layers 12 and 14.

Figure 2:
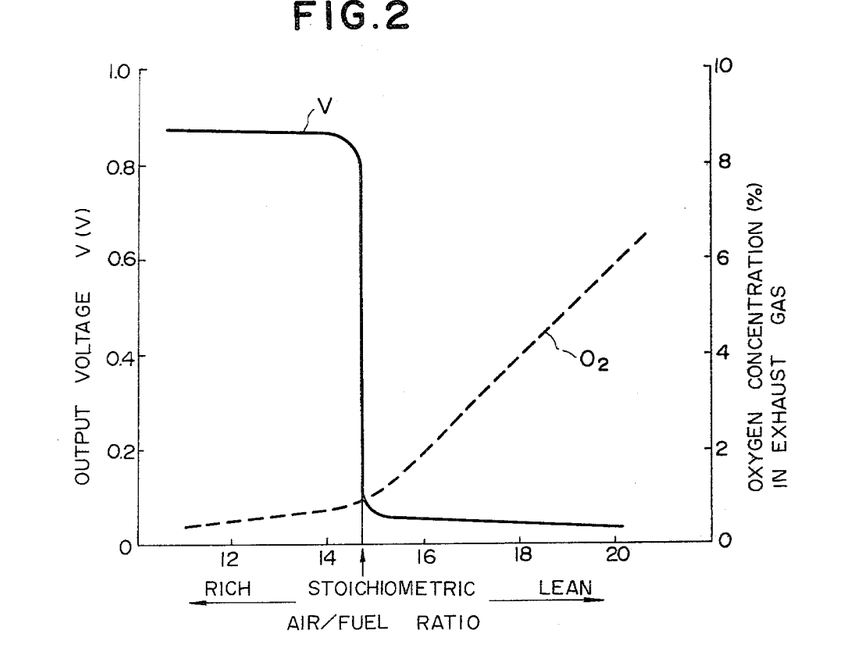
FIG. 2 is a graph showing dependence of oxygen concentration in an exhaust gas discharged from an engine and output voltage of the oxygen sensor of FIG. 1 disposed in the exhaust gas on the air/fuel ratio of an air-fuel mixture supplied to the engine.

The concentration of oxygen in the exhaust gas E depends primarily on the air/fuel ratio of an air-fuel mixture subjected to combustion in the engine and, as represented by curve $O_2$ in FIG. 2, gradually increases as the air/fuel ratio becomes higher. However, an electromotive force generated across the solid electrolyte layer 10 as output voltage V of the oxygen sensor of FIG. 1 in the exhaust gas is not proportional to the oxygen concentration in the exhaust gas. While a fuel-rich mixture is supplied to the engine, a local oxygen concentration at the surface of the measurement electrode layer 12 becomes almost zero because there occur oxidation reactions of CO, HC (unburned hydrocarbons), etc. contained in the exhaust gas at the surface of the electrode layer 12 which is made of a catalytic material such as platinum, so that a great difference in oxygen partial pressure is produced between the outer and inner sides of the solid electrolyte layer 10. Therefore, the output voltage V of the oxygen sensor remains practically constantly at a maximally high level so long as the air/fuel ratio is below a stoichiometric ratio (about 14.7 for air-gasoline mixture) as represented by curve V in FIG. 2. While a lean mixture is supplied to the engine, a difference in oxygen partial pressure between air A and the exhaust gas E becomes very small, so that the output voltage V of the sensor remains practically constantly at a minimally low level. Therefore, the output voltage of this oxygen sensor in the exhaust gas E exhibits a great and abrupt change as can be seen in FIG. 2 when the air/fuel ratio changes across the stoichiometric ratio. In other words, in the exhaust gas E this oxygen sensor exhibits an on-off type output characteristic with respect to the air/fuel ratio. The output voltage V of this oxygen sensor is affected by the temperature of the sensor, and the characteristic curve V in FIG. 2 represents experimental data obtained at a constant temperature of 600° C.

In conventional air/fuel ratio control systems which utilize an oxygen sensor of the type as shown in FIG. 1 to maintain a stoichiometric air/fuel ratio, the output voltage of the oxygen sensor is used as a feedback signal and compared with a fixed reference voltage which corresponds to the stoichiometric air/fuel ratio (for example, 500 mV in the case of the sensor output characteristic of FIG. 2). While the output voltage is higher than the reference voltage, a judgement that a fuel-rich mixture is being supplied to the engine is made, and accordingly a control signal to decrease the fuel feed rate is produced. While the output voltage of the sensor is below the reference voltage a judgement is made that a lean mixture (containing excess air) is being supplied to the engine, and a control signal to increase the fuel feed rate is produced. In practice, however, this oxygen sensor has disadvantages in several respects as mentioned hereinbefore.

Figure 3:
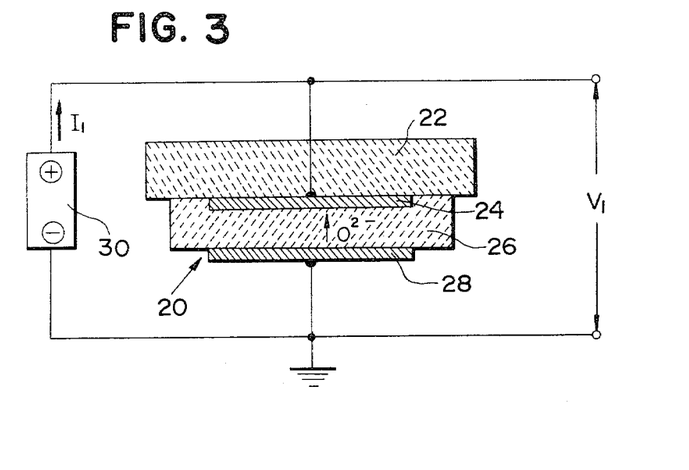
FIGS. 3 and 4 show schematically and sectionally a fundamental construction of a recently developed oxygen-sensitive element for the explanation of the principle of the function of the element.

FIG. 3 shows a fundamental construction of an advanced oxygen-sensitive element 20 disclosed in U.S. Pat. No. 4,207,159 and an air/fuel ratio detecting device using the same element. This oxygen-sensitive element 20 has a shield layer 22 which is made of an electrochemically inactive and heat-resistant material and thick enough to serve as a structurally basic member or substrate of the element 20. A reference electrode layer 24, an oxygen ion conductive solid electrolyte layer 26 and a measurement electrode layer 28 are formed on the shield layer 22 one upon another such that the reference electrode layer 24 is sandwiched between the shield layer 22 and the solid electrolyte layer 26 and, macroscopically, entirely shielded from the environmental atmosphere. The measurement electrode layer 28 on the outer side of the solid electrolyte layer 26 is made to have a microscopically porous and gas permeable structure, and at least one of the solid electrolyte layer 26 and the shield layer 22, usually the former, is made to have a microscopically porous and gas permeable structure. It will be understood that the solid electrolyte layer 26 and the two electrode layers 24, 28 constitute an oxygen concentration cell which generates an electromotive force when there is a difference in oxygen partial pressure between the reference electrode side and the measurement electrode side of the solid electrolyte layer 26. In this element 20, it is not intended to introduce a certain reference gas to the surface of the reference electrode layer 24. Instead, a DC power supply 30 is connected to the reference and measurement electrode layers 24 and 28 to force a DC current to flow through the solid electrolyte layer 26 between the two electrode layers 24 and 28 in a selected direction.

In the case of FIG. 3, the DC power supply 30 is connected to the reference and measurement electrode layers 24 and 28 such that a current $I_1$ flows through the solid electrolyte layer 26 from the reference electrode layer 24 towards the measurement electrode layer 28. When, therefore, this element 20 is disposed in an oxygen-containing gas there occurs ionization of oxygen molecules at the measurement electrode layer 28, and the formed oxygen ions migrate through the solid electrolyte layer 26 towards the reference electrode layer 24. The oxygen ions arriving at the reference electrode layer 24 are converted to oxygen molecules, so that there is a tendency that oxygen accumulates on the reference electrode side of the solid electrolyte layer 26 with a resultant rise in oxygen partial pressure on this side. However, the accumulated oxygen continues to flow out through the porous solid electrolyte layer 26. Therefore, a nearly constant oxygen partial pressure is established at the interface between the reference electrode layer 24 and the solid electrolyte layer 26 after the lapse of a short period of time. Then the concentration cell in the element 20 generates an electromotive force indicative of an oxygen partial pressure at the measurement electrode layer 28 relative to the nearly constant oxygen pressure established at the reference electrode layer 24. An output voltage $V_1$ attributed to this electromotive force can be measured between the reference and measurement electrode layers 24 and 28.

Figure 5:
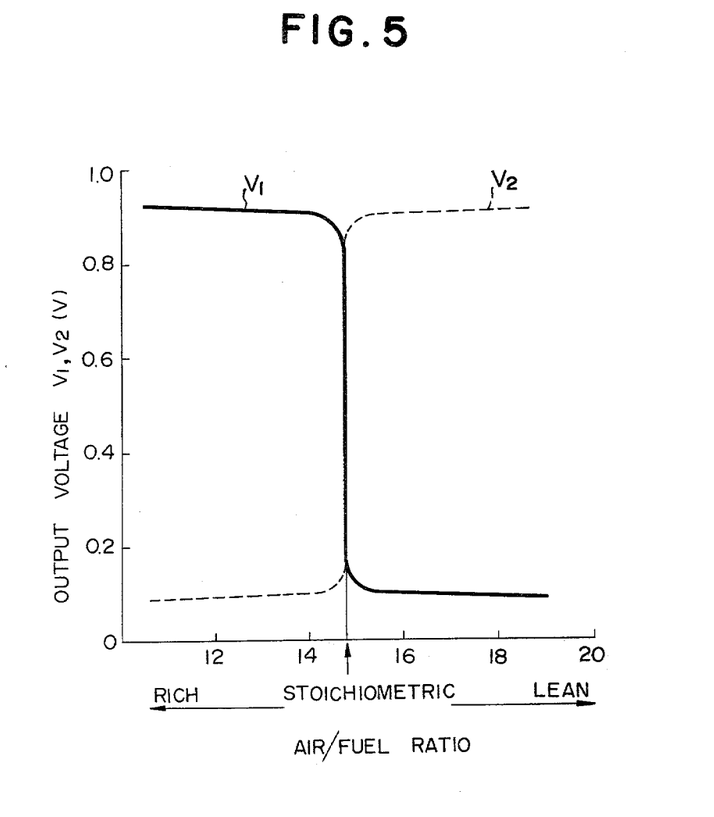
FIG. 5 is a graph showing output characteristics of the oxygen-sensitive element of FIGS. 3 and 4 in an engine exhaust gas.

When this element 20 is disposed in an exhaust gas of an internal combustion engine and supplied with a DC current of an appropriate intensity as shown in FIG. 3, the output voltage $V_1$ becomes either considerably high or very low in accordance with the engine being fed with a rich mixture or a lean mixture. While a rich mixture is fed to the engine, the supply of oxygen to the reference electrode layer 24 by migration of oxygen ions thereto produces a considerable effect compared with the relatively small inward diffusion of gaseous oxygen contained in the exhaust gas through the porous solid electrolyte layer 24. The magnitude of a constant reference oxygen partial pressure established on the reference electrode side depends on various factors such as the exhaust gas temperature, intensity of the DC current $I_1$ and the thickness and structure of the solid electrolyte layer 24. By way of example, a reference oxygen partial pressure of $10^0$–$10^2$ atm is established when the exhaust gas temperature is 600° C. and the current intensity is 3 $\mu$A, whereas the oxygen partial pressure in the exhaust gas is $10^{-2}$–$10^{-3}$ atm. Accordingly, while a rich mixture is fed to the engine the output voltage $V_1$ remains at a considerably high level as represented by curve $V_1$ (solid line) in FIG. 5. However, when a lean mixture is fed to the engine the effect of the migration of oxygen ions to the reference electrode 24 becomes relatively small compared with inward diffusion of an increased quantity of gaseous oxygen through the solid electrolyte layer 26. As a consequence the difference between the reference oxygen partial pressure on the reference electrode side and the oxygen partial pressure in the exhaust gas becomes very small, so that the output voltage $V_1$ remains at a very low level as shown in FIG. 5. Accordingly, a great and rapid change occurs in the level of the output voltage $V_1$ when the air/fuel ratio of a mixture supplied to the engine changes across the stoichiometric ratio. Therefore, the device of FIG. 3 can serve the same function as the conventional oxygen sensor of FIG. 1 in a combustion gas.

Figure 4:
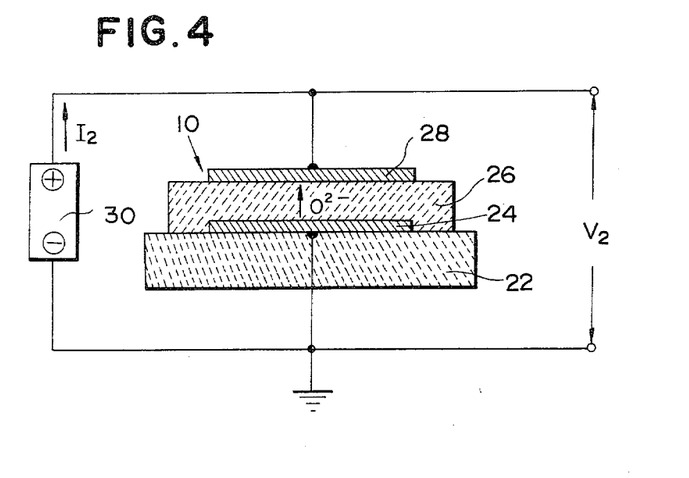

FIG. 4 shows another case where the DC power supply 30 is connected to the reference and measurement electrode layers 24 and 28 of the oxygen-sensitive element 20 such that a DC current $I_2$ flows through the solid electrolyte layer 26 from the measurement electrode layer 28 towards the reference electrode layer 24. In this case, oxygen molecules diffused to the reference electrode layer 24 are ionized at this electrode layer 24, and the formed oxygen ions migrate outwardly through the solid electrolyte layer 26. At the measurement electrode layer 28, the oxygen ions are converted to gaseous oxygen which is liberated into the exterior gas atmosphere. Therefore, there is a tendency toward lowering the oxygen partial pressure on the reference electrode side of the solid electrolyte layer 26. Balanced by inward diffusion of oxygen molecules through the solid electrolyte layer, soon a nearly constant and relatively low oxygen partial pressure is established at the interface between the reference electrode layer 24 and the solid electrolyte layer 26. In an exhaust gas discharged from an internal combustion engine operated with a lean mixture, the magnitude of the thus established reference oxygen partial pressure becomes $10^{-20}-10^{-22}$ atm, for example, when the exhaust gas temperature is 600° C. and the intensity of the DC current $I_2$ is 3 $\mu$A. Accordingly output voltage $V_2$ of the element 20 in this case remains at a considerably high level as represented by curve $V_2$ (broken line) in FIG. 5. When a rich mixture is supplied to the engine, the output voltage $V_2$ remains at a very low level as shown in FIG. 5 because ionization of oxygen at the reference electrode layer 24 becomes insignificant by reason of a great decrease in the quantity of gaseous oxygen inwardly diffusing through the solid electrolyte layer 26. Therefore, also in this case a great and rapid change occurs in the level of the output voltage $V_2$ when the air/fuel ratio of a mixture supplied to the engine changes across the stoichiometric ratio.

Either in the case of FIG. 3 or in the case of FIG. 4, it is desirable that the DC power supply 30 is of a constant current type so that the current $I_1$ or $I_2$ forced to flow through the solid electrclyte layer 26 between the two electrode layers 24 and 28 is a constant current.

Figure 6:
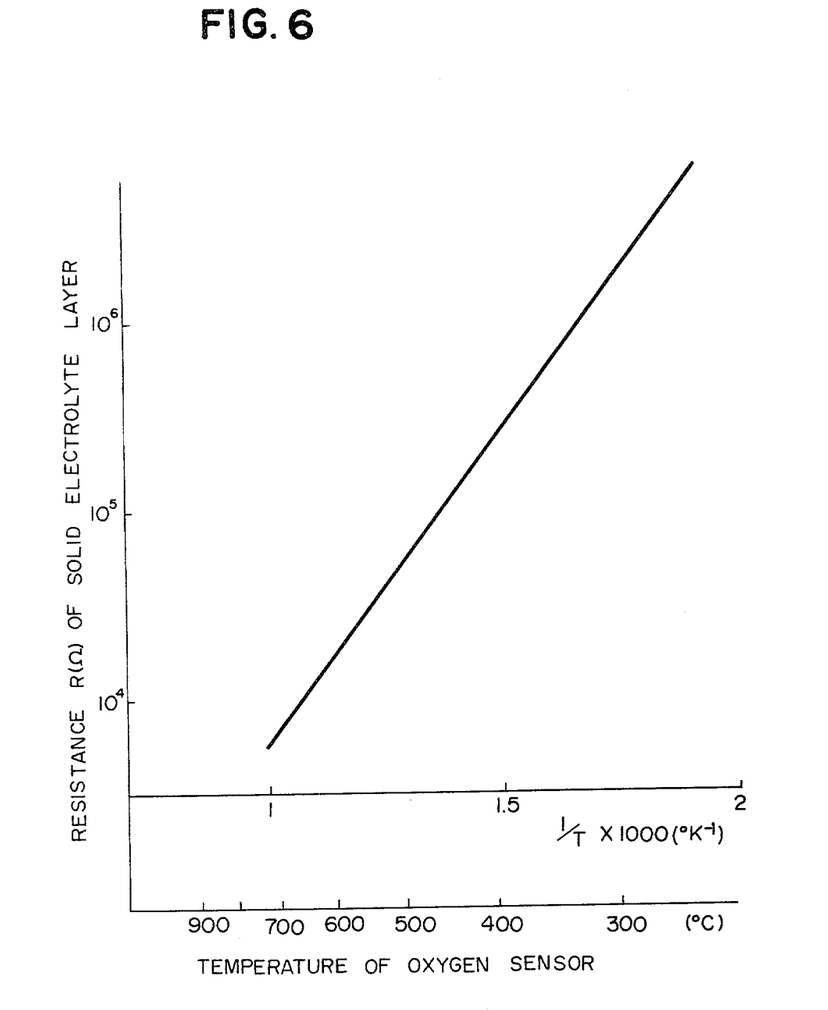
FIG. 6 is a graph showing the dependence of the electrical resistance of a solid electrolyte layer in the oxygen-sensitive element of FIGS. 3 and 4 on temperature.
Figure 7:
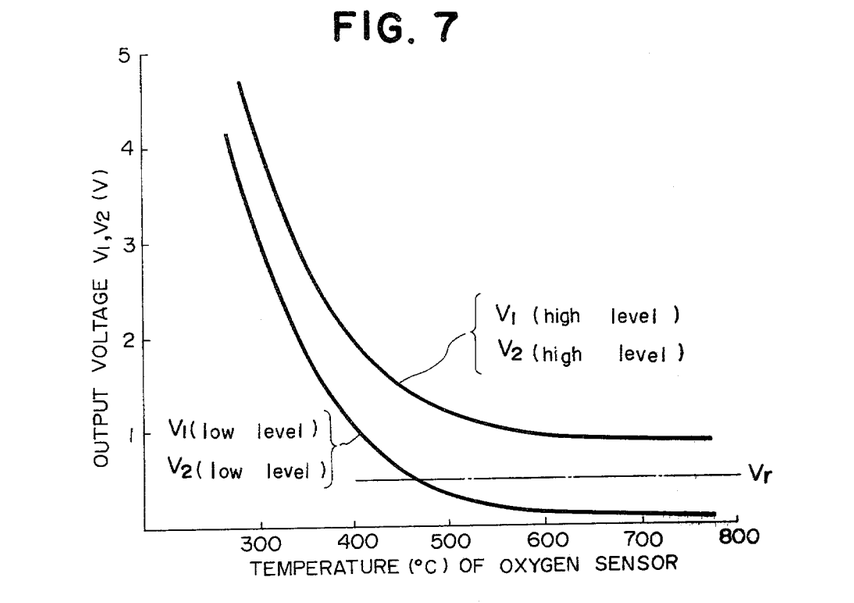
FIGS. 7 and 8 are graphs showing the dependence of the output voltage of the oxygen-sensitive element of FIGS. 3 and 4 in an engine exhaust gas on the temperature of the element.
Figure 8:
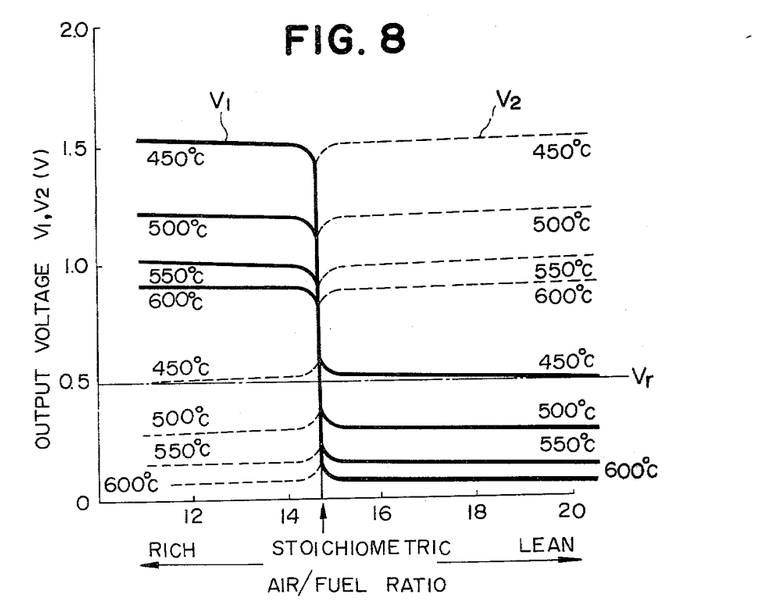

In the device of either FIG. 3 or FIG. 4, the DC power supply 30 and a voltage measuring instrument (not shown) are both connected between the reference and measurement electrode layers 24 and 28. Accordingly the output voltage $V_1$ or $V_2$ of the oxygen-sensitive element 20 becomes the sum of an electromotive force the element 20 generates and a voltage developed across the solid electrolyte layer 26, which has an electrical resistance R, by the flow of the constant current $I_1$ or $I_2$ therethrough, that is, a voltage expressed by $I_1 \times R$ or $I_2 \times R$. The resistance R of the solid electrolyte layer 26 depends significantly on the temperature of the element 20 as shown exemplarily in FIG. 6; the resistance R greatly increases as the temperature of the element 20 lowers. Therefore, the output voltage $V_1$ or $V_2$ is significantly affected by the temperature of the element 20. As shown in FIGS. 7 and 8, there is a tendency that the output voltage $V_1$ or $V_2$ becomes higher as the temperature lowers, and this tendency becomes very strong when the temperature is below a certain level, for example below about 550° C.

In performing feedback control of air/fuel ratio in an internal combustion engine by using the device of FIG. 3 or FIG. 4, it will be natural to compare the output voltage $V_1$ or $V_2$ with a fixed reference voltage $V_r$ of 0.5 V if a normal output characteristic of the device of FIG. 3 or 4 is as shown in FIG. 5. FIGS. 7 and 8 show that if the temperature of the oxygen-sensitive element 20 is below 450° C. the output voltage $V_1$ or $V_2$ remains above the reference voltage $V_r$ whether a rich mixture or a lean mixture is supplied to the engine, meaning that the feedback control of air/fuel ratio becomes impossible. In other words, stable operation of a feedback air/fuel ratio control system including the device of FIG. 3 or 4 is difficult while the temperature of the element 20 or exhaust gas temperature is below, for example, about 550° C.

As mentioned hereinbefore, the present invention solves this problem by making the best use of the essential features of the advanced oxygen-sensitive element.

Figure 9:
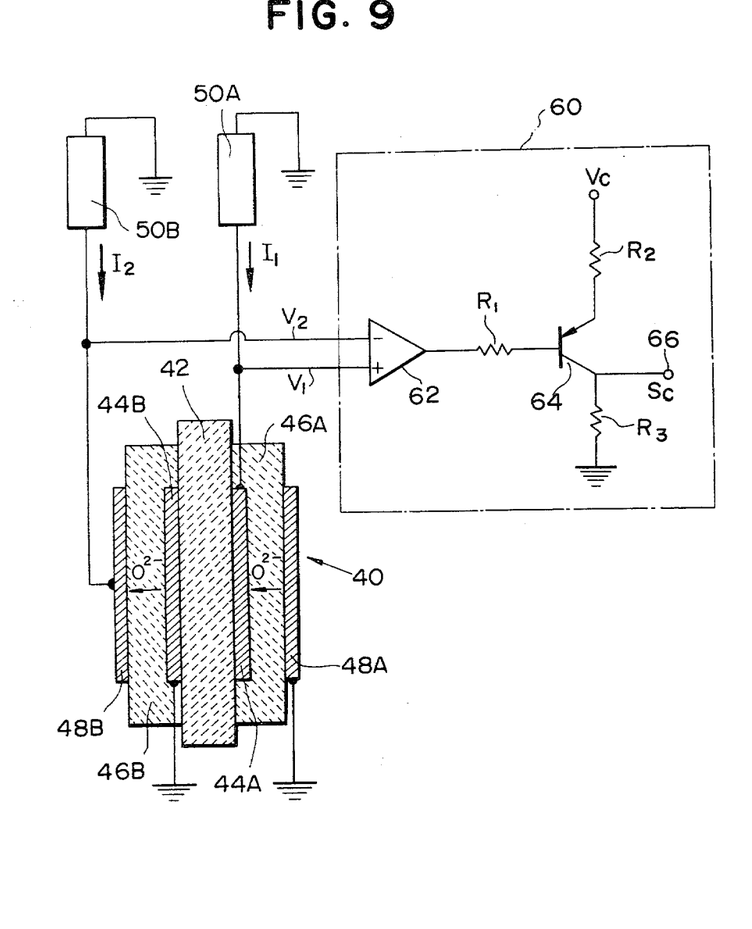
FIG. 9 is a schematic and partly sectional illustration of a control signal producing device as an embodiment of the present invention.

FIG. 9 shows an air/fuel ratio control signal producing device as an embodiment of the present invention. Essentially this device is constituted of an oxygen-sensitive element 40, a set of DC power supplies 50A and 50B, and a signal-producing circuit 60.

The oxygen-sensitive element 40 has a shield layer 42 which is rigid and thick enough to serve as a substrate of this element 40. On one side of the shield layer 42, a first reference electrode layer 44A, a first oxygen ion conductive solid electrolyte layer 46A and a first measurement electrode layer 48A are formed one upon another such that macroscopically the reference electrode layer 44A is entirely shielded from the environmental atmosphere by the shield layer 42 and the solid electrolyte layer 46A. Each of the three layers 44A, 46A and 48A is a thin film-like layer, and the measurement electrode layer 48A and the solid electrolyte layer 46A are both microscopically porous and gas permeable. On the opposite side of the shield layer 42, a second reference electrode layer 44B, a second oxygen conductive solid electrolyte layer 46B and a second measurement electrode layer 48B are formed one upon another generally symmetrically with the corresponding layers 44A, 46A and 48A on the other side. Macroscopically te second reference electrode layer 44B is entirely shielded from the environmental atmosphere, and the second measurement electrode layer 48B and second solid electrolyte layer 46B are microscopically porous and gas permeable.

Thus, this element 40 can be regarded as a combination of two sets of oxygen concentration cells: that is, one constituted of the first solid electrolyte layer 46A, the first reference and measurement electrode layers 44A, 48A and the shield layer 42; and the other constituted of the second solid electrolyte layer 46B, the second reference and measurement electrode layers 44B, 48B and the shield layer 42 which is utilized by the two cells in common.

A first DC power supply 50A, preferably of a constant current type, is connected to the reference and measurement electrode layers 44A and 48A of the first cell so as to force a DC current $I_1$ of a predetermined intensity to flow through the first solid electrolyte layer 46A from the reference electrode layer 44A towards the measurement electrode layer 48A. A second DC power supply 50B preferably of a constant current type is connected to the electrode layers 44B and 48B of the second cell so as to force a DC current $I_2$ of a predetermined intensity to flow through the second solid electrolyte layer 46B from the measurement electrode layer 48B towards the reference electrode layer 44B. Accordingly, when the oxygen-sensitive element 40 is disposed in an oxygen-containing gas such as an engine exhaust gas there occurs ionization of oxygen at the first measurement electrode layer 48A, and the formed oxygen ions migrate through the first solid electrolyte layer 46A towards the first reference electrode layer 44A, whereas in the cell on the opposite side oxygen ions migrate through the second solid electrolyte layer 46B from the reference electrode layer 44B towards the measurement electrode layer 48B.

The circuit 60 has a comparator 62 and a switching transistor 64. The positive input terminal of this comparator 62 is connected to the first reference electrode layer 44A of the oxygen-sensitive element 40 to receive an output voltage $V_1$ of the first concentration cell, and the negative input terminal of the comparator is connected to the second measurement electrode layer 48B to receive an output voltage $V_2$ of the second concentration cell. The output terminal of the comparator 62 is connected to the base of the switching transistor 64 via a resistance $R_1$. A source voltage $V_c$ is applied to the collector of the transistor 64 through a resistance $R_2$, and the emitter of this transistor 64 is grounded through a resistance $R_3$. When the transistor 64 is conducting, the resistances $R_2$ and $R_3$ constitute a voltage divider. Connected to an output terminal of the voltage divider on the emitter side in an output terminal 66 of the circuit 60.

In the device of FIG. 9, the first concentration cell (comprising the first solid electrolyte layer 46A) corresponds to the element 30 in FIG. 3, and the second concentration cell (comprising the second solid electrolyte layer 46B) corresponds to the element 30 in FIG. 4. When the oxygen-sensitive element 40 in FIG. 9 is disposed in an exhaust gas of a gasoline engine the first concentration cell exhibits an output characteristic as represented by curve $V_1$ in FIG. 5, while the second cell exhibits an output characteristic represented by curve $V_2$ in FIG. 5. If a rich mixture is supplied to the engine the output voltage $V_1$ of the first cell becomes far greater than the output voltage $V_2$ of the second cell, meaning that the comparator 62 receives a greater input at its positive input terminal than at the negative input terminal. Accordingly the comparator 62 provides an output voltage to the base of the switching transistor 64 so that the transistor 64 becomes conducting and provides a control signal $S_c$ of a predetermined voltage to the output terminal 66. For example, when the source voltage $V_c$ is 12 V, resistance $R_2$ is 11 k$\Omega$ and resistance $R_3$ is 1 k$\Omega$, the amplitude of the control signal $S_c$ becomes 1 V. This control signal $S_c$ is supplied to a fuel feed regulating means (not shown) to decrease the fuel feed rate until the stoichiometric air/fuel ratio is realized. If a lean mixture is supplied to the engine the output voltage $V_1$ of the first cell becomes far lower than the output voltage $V_2$ of the second cell, meaning that the comparator 62 receives a greater input at its negative input terminal than at the positive input terminal. Accordingly the comparator 62 stops producing an output, so that the transistor 64 becomes nonconducting. Therefore, the control signal $S_c$ at the output terminal 66 becomes a zero volt signal, which causes the fuel feed regulating means to increase the fuel feed rate until the stoichiometric air/fuel ratio is realized.

Both of the output voltages $V_1$ and $V_2$ depend on the temperature of the oxygen-sensitive element 40, and as the temperature lowers both of these output voltages $V_1$ and $V_2$ become similarly higher. Accordingly, a highlow relationship between the two output voltages $V_1$ and $V_2$ remains unchanged even though the temperature becomes as low as 450° C. by way of example to cause a great rise of the maximal level of each output voltage $V_1$, $V_2$, as will be understood by reference to FIGS. 7 and 8. In a feedback control system including the signal-producing device of FIG. 9, it is unnecessary to use a fixed reference voltage corresponding to the reference voltage $V_r$ in FIGS. 7 and 8. Thus, by utilizing the device of FIG. 9 it becomes possible to stably perform feedback control of air/fuel ratio, aiming at a stoichiometric ratio, without the control being unfavorably influenced by changes in the temperature of the sensitive element 40 or exhaust gas in which the element 40 is disposed.

Figure 10:
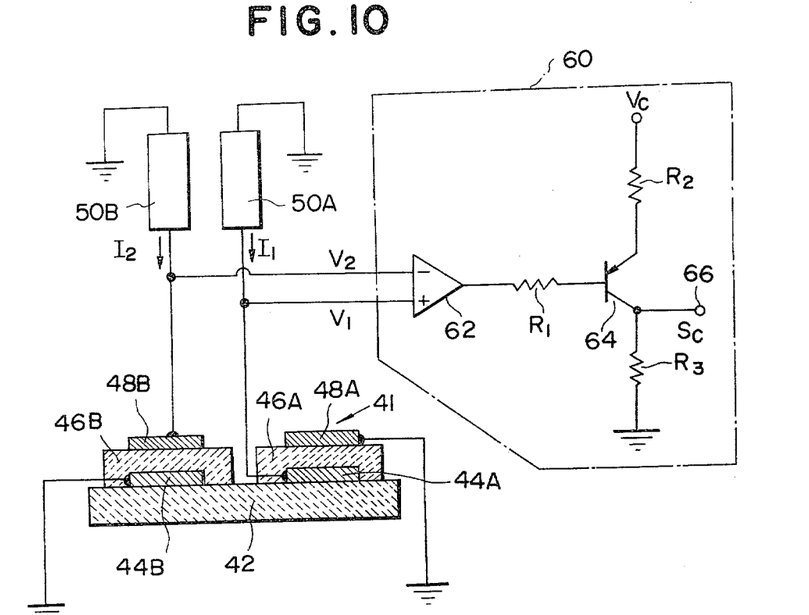
FIGS. 10-13 show, each in a view similar to FIG. 9, four differently designed devices embodying the present invention, respectively.

FIG. 10 shows another embodiment of the present invention. An oxygen-sensitive element 41 is this signal-producing device is similar in principle to the element 40 in FIG. 9 but different in the arrangement of the two oxygen concentration cells. The combination of the first reference electrode layer 44A, first solid electrolyte layer 46A and first measurement electrode layer 48A is formed so as to occupy a limited portion of the surface area of the shield layer 42. Spaced from this combination, but on the same side of the shield layer 42, the combination of the second reference electrode layer 44B, second solid electrolyte layer 46B and second measurement electrode layer 48B is formed similarly to the first combination of the three layers 44A, 46A and 48A. The shield layer 42 is common to the two concentration cells and serves also as the substrate of the entire element 41.

In other respects, the device of FIG. 10 is constructed identically with the device of FIG. 9. The first DC power supply 50A is connected to the first cell of the oxygen-sensitive element 41 so as to force a constant DC current $I_1$ to flow through the first solid electrolyte layer 46A from the first reference electrode layer 44A towards the first measurement electrode layer 48A. The second DC power supply 50B is connected to the second cell so as to force a constant current $I_2$ to flow through the second solid electrolyte layer 46B from the measurement electrode layer 48B towards the reference electrode layer 44B. The output voltage $V_1$ of the first cell and the output voltage $V_2$ of the second cell are applied respectively to the positive and negative input terminals of the comparator 62 of the signal-producing circuit 60. Therefore, the function of the device of FIG. 10 with the oxygen-sensitive element 41 disposed in a combustion gas is identical with the function of the device of FIG. 9.

Figure 11:
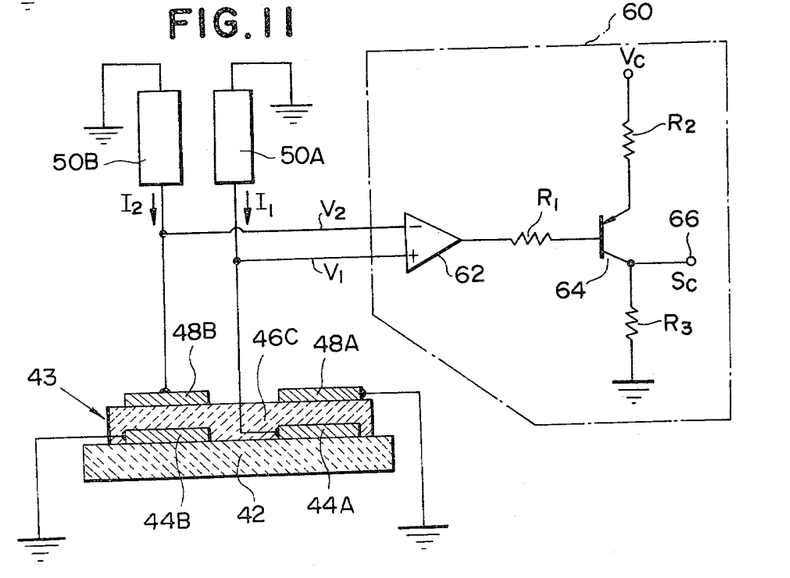

FIG. 11 shows a signal-producing device which is almost identical with the device of FIG. 10. As a sole modification, oxygen-sensitive element 43 in this device has a single solid electrolyte layer 46C which can be regarded as the union of the first and second solid electrolyte layers 46A and 46B in the element 41 of FIG. 10. That is, a part of this solid electrolyte layer 46C intervening between first reference and measurement electrode layers 44A and 48A is utilized to constitute the first concentration cell and another part intervening between the second reference and measurement electrode layers 44B and 48B is utilized to consititute the second cell. Of course, the first and second reference electrode layers 44A and 44B are spaced from each other, and the first and second measurement electrode layers 48A and 48B are spaced from each other. It will be understood that the device of FIG. 11 functions identically with the devices of FIGS. 9 and 10.

Figure 12:
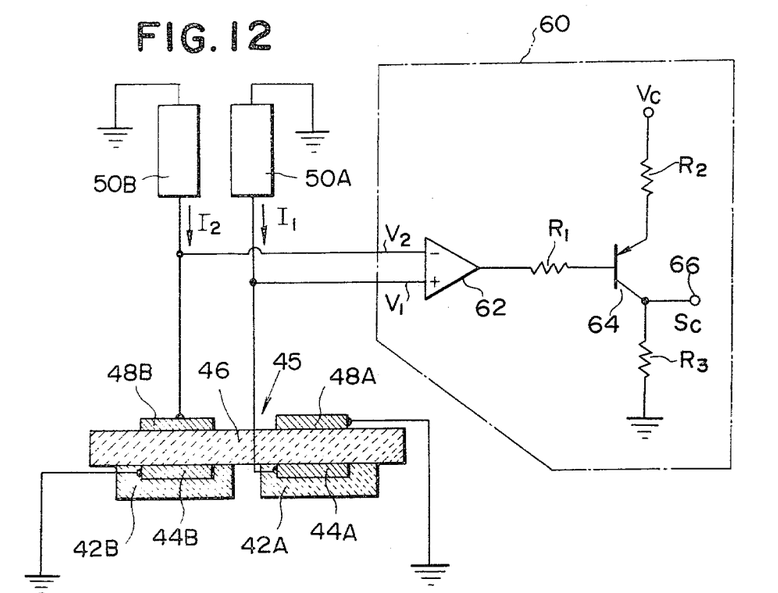

FIG. 12 shows a still another embodiment of the invention. An oxygen-sensitive element 45 in this signal-producing device has a single solid electrolyte layer 46 which is in the form of a rigid plate thick enough to serve also as a structurally basic member or substrate of this element 45. On one side of this solid electrolyte layer 46, a thin first reference electrode layer 44A and a thin second reference electrode layer 44B are formed with a distance therebetween. On the same side of the solid electrolyte layer 46, a first shield layer 42A is formed so as to entirely cover the first reference electrode layer 44A, and a second shield layer 42B to entirely cover the second reference electrode layer 44B. On the opposite side of the solid electrolyte layer 46, first measurement electrode layer 48A is formed so as to occupy a limited area and lie generally opposite to the first reference electrode layer 44A. On the same side, second measurement electrode layer 48B is formed so as to be spaced from the first measurement electrode layer 48A and lie generally opposite to the second reference electrode layer 44B. Also in this case the solid electrolyte layer 46 may be made microscopically porous. Alternatively, this solid electrolyte layer 46 may be made to have a tight, dense and practically gas impermeable structure, conditioning that then the first and second shield layers 42A and 42B are made microscopically porous and gas impermeable. When the solid electrolyte layer 46 is gas impermeable but the shield layers 42A, 42B are gas permeable, the reference electrode layers 44A, 44B are also made gas permeable. Thus, this oxygen-sensitive element 45 also comprises two sets of oxygen concentration cells.

Aside from the described difference in design of the oxygen-sensitive element 45, the device of FIG. 12 is constructed identically with the device of FIG. 9 and, therefore, has the same function as the device of FIG. 9.

Figure 13:
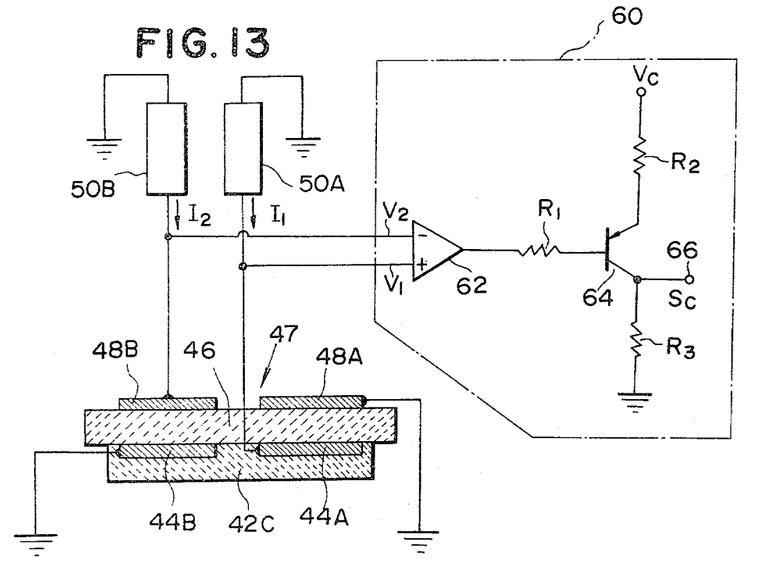

FIG. 13 shows a modification of the oxygen-sensitive element 45 of FIG. 12. Oxygen-sensitive element 47 of FIG. 13 is made by uniting the first and second shield layers 42A and 42B in FIG. 12 into a single shield layer 42C which covers both the first and second reference electrode layers 44A and 44B. Where the solid electrolyte layer 46 has a gas impermeable structure, this shield layer 42C is made to have a microscopically porous and gas permeable structure. In other respects, the device of FIG. 13 is identical with the device of FIG. 12 in construction and function.

For every one of the oxygen-sensitive elements shown in FIGS. 9-13, it is optional to provide a porous protective coating which covers the first and second measurement electrode layers 48A, 48B if desired together with the outer surfaces of the solid electrolyte layer(s), or even the entire outer surfaces of the element.

The material for each solid electrolyte layer 46, 46A, 46B, 46C can be selected from oxygen ion conductive solid electrolyte materials used for conventional oxygen sensors of the concentration cell type. Some examples are $ZrO_2$ stabilized with CaO, $Y_2O_3$, SrO, MgO, $ThO_2$, $WO_3$ or $Ta_2O_5$; $Bi_2O_3$ stabilized with $Nb_2O_5$, SrO, $WO_3$, $Ta_2O_5$ or $Y_2O_3$; and $Y_2O_3$ stabilized with $ThO_2$ or CaO. In the case of using the solid electrolyte layer 46 as the substrate of the oxygen-sensitive element as in FIGS. 12 and 13, this layer 46 may be produced, for example, by sintering of a press-molded powder material or sintering of a so-called green sheet obtained by molding or extrusion of a wet composition comprising a powdered solid electrolyte material as the principal component. Where the shield layer 46 is used as the substrate of the oxygen-sensitive element, each solid electrolyte layer 46A, 46B, 46C may be formed as a thin film-like layer by a physical deposition technique such as sputtering or ion plating, or by an electrochemical technique typified by plating, or by a process having the steps of printing a paste containing a powdered solid electrolyte material onto the substrate and then firing the paste-applied substrate.

Each shield layer 42, 42A, 42B, 42C is usually made of an electrically insulating ceramic material such as alumina, mullite, spinel or forsterite. When made to serve as the substrate of the oxygen-sensitive element, the shield layer 42 is produced, for example, by sintering of either a green sheet or a press-formed powder material, or by machining of a body of a selected material. Where the solid electrolyte layer 46 is used as the substrate, each shield layer 42A, 42B, 42C may be formed as a relatively thin film-like layer, for example, by a physical deposition technique, by plasma spraying or by the steps of printing a paste containing a powdered ceramic material onto the substrate and then sintering the printed paste layer.

Each of the reference and measurement electrode layers 44A, 44B, 48A, 48B is made of an electronically conductive material selected from electrode materials for conventional solid electrolyte oxygen sensors. Examples are metals of the platinum group, which exhibit a catalytic action on oxidation reactions of hydrocarbons, carbon monoxide, etc., such as Pt, Pd, Ru, Rh, Os and Ir, including alloys of these platinum group metals and alloys of a platinum group metal with a base metal, and some other metals and oxide semiconductors such as Au, Ag, SiC, $TiO_2$, CoO and $LaCrO_3$ which do not catalyze the aforementioned oxidation reactions. Each electrode layer is formed on a shield layer or a solid electrolyte layer as a relatively thin film-like layer, for example, by a physical deposition technique such as sputtering or ion plating, or by an electrochemical technique typified by plating, or by printing of a paste containing a powdered electrode material, followed by firing of the paste-applied shield layer and/or solid electrolyte layer.

For the aforementioned porous protective coating, use may be made of a heat-resistant and electrically insulating material such as alumina, spinel, mullite or calcium zirconate ($CaO-ZrO_2$). The porous protective coating may be produced, for example, by plasma spraying or by the steps of immersing the oxygen-sensing element in a slurry of a selected powder material, drying the slurry adhered to the element and then firing the thus treated element.

What is claimed is:

1. A device to produce a control signal for feedback control of the air/fuel ratio of an air-fuel mixture supplied to a combustor, the device comprising:
   an oxygen-sensitive element which is to be disposed in a combustion gas exhausted from the combustor and comprises first and second oxygen concentration cells each comprising of a layer of an oxygen ion conductive solid electrolyte; a measurement electrode layer formed on one side of the solid electrolyte layer; a reference electrode layer formed on the other side of the solid electrolyte layer and a shield layer formed on the reference electrode layer; side of the solid electrolyte layer such that macroscopically the reference electrode layer is entirely shielded from an environmental atmosphere by the shield layer and the solid electrolyte layer, at least one of the solid electrolyte layer and the shield layer of each concentration cell having a microscopically porous and gas permeable structure;

DC power supply means for forcing a first DC current of a predetermined intensity to flow through the solid electrolyte layer of the first cell from the reference electrode layer towards the measurement electrode layer and a second DC current of a predetermined intensity to flow through the solid electrolyte layer of the second cell from the measurement electrode layer towards the reference electrode layer; and a signal-producing circuit having comparing means for making a comparison between a first output voltage developed between the reference and measurement electrode layers of the first cell and a second output voltage developed between the reference and measurement electrode layers of the second cell to examine which one of the first and second output voltages is higher than the other, and signal-generating means for producing said control signal which varies according to a high-low relationship between the first and second output voltages examined by the comparing means.

2. A device according to claim 1, wherein the shield layer of the first cell and the shield layer of the second cell are united into a single shield layer which is so shaped and dimensioned as to serve as a structurally basic member of the oxygen-sensitive element.

3. A device according to claim 2, wherein the reference electrode layer of the first cell lies on one side of said single shield layer whereas the reference electrode layer of the second cell lies on the opposite side of said single shield layer such that the first and second cells are arranged generally symmetrically with respect to a middle plane in said single shield layer.

4. A device according to claim 2, wherein the reference electrode layer of the first cell and the reference electrode layer of the second cell lie on the same side of said single shield layer such that the first and second cells are arranged generally symmetrically with respect to a plane perpendicular to said single shield layer.

5. A device according to claim 4, wherein the solid electrolyte layer of the first cell and the solid electrolyte layer of the second cell are united into a single solid electrolyte layer.

6. A device according to claim 1, wherein the solid electrolyte layer of the first cell and the solid electrolyte layer of the second cell are united into a single solid electrolyte layer which is so shaped and dimensioned as to serve as a structurally basic member of the oxygen-sensitive element.

7. A device according to claim 6, wherein the shield layer of the first cell and the shield layer of the second cell are united into a single shield layer.

8. A device according to claim 1, wherein each of the first and second DC currents is a constant current.

9. A device according to claim 1, wherein the signal-generating means of said circuit comprise a switching transistor the base of which is electrically connected to said comparing means such that an output voltage is provided from said comparing means to the base of said transistor when a predetermined one of said first and second output voltages is higher than the other.

10. A device according to claim 9, wherein said signal-generating means comprise a voltage divider to which is applied a source voltage when said switching transistor is in the conducting state, said control signal being based on a voltage at an output terminal of said voltage divider.

* * * * *